United States Patent [19]

Fiala

[11] Patent Number: Plant 7,022

[45] Date of Patent: Sep. 12, 1989

[54] CRABAPPLE TREE NAMED RED PEACOCK

[75] Inventor: John L. Fiala, Medina, Ohio

[73] Assignee: Chas. Klehm & Son, South Barrington, Ill.

[21] Appl. No.: 213,605

[22] Filed: Jun. 30, 1988

[51] Int. Cl.[4] ..... A01H 5/00

[52] U.S. Cl. ..... Plt./34

[58] Field of Search ..... Plt./34

*Primary Examiner*—James R. Feyrer

*Attorney, Agent, or Firm*—Foley & Lardner, Schwartz et al.

[57] ABSTRACT

An ornamental flowering crabapple tree named Red Peacock, having large coral buds opening to soft pink and white ruffled blossoms, mint green disease free foliage, abundant annual blossoms and shiny red berries, early uprightness tending toward maturity into a semi-weeping habit, tannish gold bark and stems, and fruit maintenance into early winter.

4 Drawing Sheets

The present invention comprises a new and distinct cultivar of crabapple tree, botanically known as Malus, and hereinafter referred to by the cultivar name Red Peacock.

The new cultivar, discovered by the inventor in 1969, resulted from a controlled cross by the inventor of seed parent Malus 'Molton Lava' with pollen parent (Malus 'Luwick'×Malus Zumi #243) in Medina, Ohio. Asexual reproduction by the inventor in the form of rooted cuttings and summer chip budding taken in Medina, Ohio has demonstrated that the combination of characteristics as herein disclosed for the new cultivar are firmly fixed and are retained through successive generations of asexual reproduction.

Red Peacock has not been observed under all possible environmental conditions. The phenotype may vary significantly with variations in environment such as temperature, light intensity, day length, available soil moisture, soil nutrients and $p^H$ level.

The following observations, measurements and comparisons describe trees grown at Klehm Nursery, Barrington, Ill., under conditions which approximate those generally used in commercial practice.

The following repeatedly observed traits characteristic Red Peacock. These traits, in combination, distinguish this crabapple tree as a new and distinct cultivar:

1. Red Peacock produces large coral-pink buds that open to soft pink to white ruffled blossoms. It is an abundant, annual bloomer.
2. Its well textured, mint green, disease free foliage is light and airy in appearance.
3. It produces shiny red berries in abundance.
4. Red Peacock is upright when young, becoming somewhat semi-weeping towards maturity.
5. It possesses tannish gold bark and stems.
6. Its early winter fruit is maintained on the tree until consumed by birds.

Of the many commercial crabapple trees known to the inventor, the most similar in comparison to Red Peacock is Sentinel. In comparison to Sentinel, Red Peacock has a more graceful growth habit, brighter colored fruit and larger, more ruffled blossoms.

The accompanying color photographic drawings show typical characteristics of Red Peacock, with colors being as true as possible with illustrations of this type. Sheet 1 is a color photograph of Red Peacock in full blossom. Sheet 2 is a color photograph of a branch of Red Peacock showing unopened blossoms. Sheet 3 is a color photograph of a branch of Red Peacock showing both opened and unopened blossoms, with blossom and leaf color depicted. Sheet 4 is a color photograph of mature fruit of Red Peacock.

In the following detailed description color references are made to The Royal Horticultural Society Colour Chart (RHS).

TREE

Origin: Seedling.

Parentage:

*Seed parent.*—'Molton Lava'.

*Pollen parent.*—(Luwick×Malus Zumi #243).

Classification:

*Botanic.*—Malus×cv Red Peacock. '*Commercial*.—Ornamental flowering crabapple.

Propagation: Chip budding, bench grafting or softwood cuttings.

Size: A fully mature tree at 30 years will reach 20 to 25 feet high with a spreading diameter of up to 20 feet; excellent growth habit.

Branches: Slender, somewhat spreading to semi-weeping with graceful branchlets.

Color: Winter color of new growth is olive green, summer color medium green; bark is tannish gold to a fully mature dark brown, somewhat exfoliating with maturity.

Leaves: Lanceolate in shape and up to 6 cm in length, with margins smooth to incised; dark green upper surface, medium green lower surface; thick, and highly disease resistant; leaf petiole very small.

FLOWERS

Buds:

*Color.*—Coral pink.

*Size.*—Large.

*Quantity.*—Very abundant.

Blossoms:

*Size.*—Large, approximately 1-1.25" in diameter, and ruffled.

*Quantity.*—Greatly abundant; the combination of buds and open blossoms make for a tree of cascading beauty and is unique as a semi-weeper; blooms annually.

*Color.*—Coral-pink when opening, becoming soft pink 36D to white when fully open.

Date of first bloom: Normally May 10-15.

Date of full bloom: Normally May 15–20.

FRUIT

Date of maturity: October 15.
Shape: Round, relatively small, 5/16 to ⅜" in diameter.
Quantity: Very heavy fruit producer.
Hardness: Firm.
Color: Shiny orange-red, 43A-B, providing an excellent contrast with the clear green autumn foliage.
Keeping quality: Excellent; when leaves fall, the tree is a unique display of slender semi-weeping branchlets covered with a tremendous display of glowing fruit; fruit holds well into winter or until eaten by birds.
Bruise resistant: Excellent
Insect and disease resistance: Rated high for resistance to common crabapple diseases apple scab, cedar-apple rust, fire blight, frog-eye leaf spot, and powdery mildew.

General observations: Due to its form and prolific flowering/fruiting habit, Red Peacock is very unique and readily distinguishable from other flowering crab varieties. Red Peacock grows well in ordinary soils, and is especially well suited for smaller landscapes where heavy blossoms and an abundant display of bright orange-red fruit is desired. There is no messy fall fruit drop, and the small fruit is eaten quickly by birds in late winter.

I claim:

1. A new and unique flowering crabapple tree named Red Peacock, as illustrated and described.

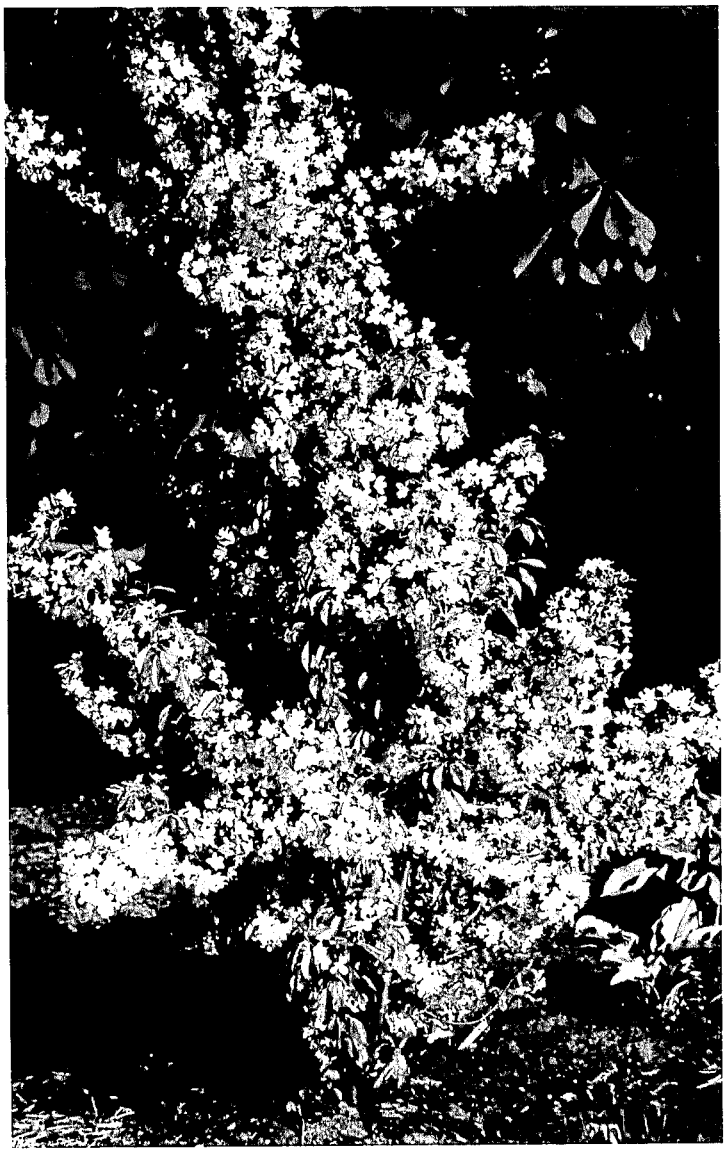

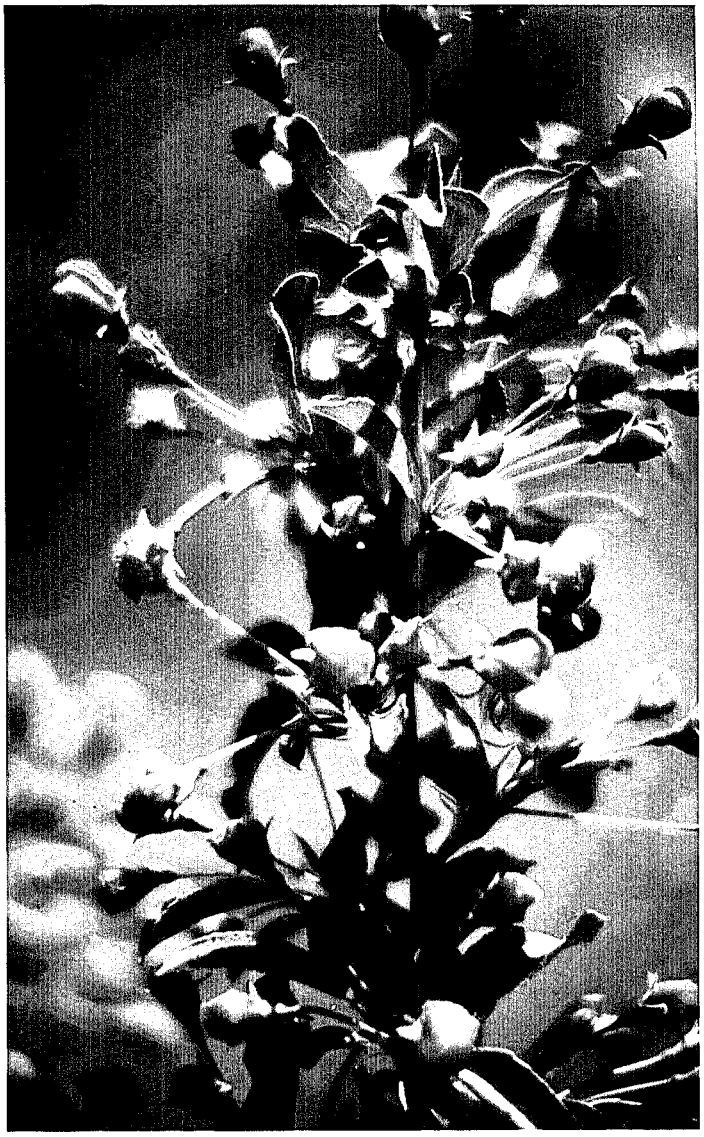

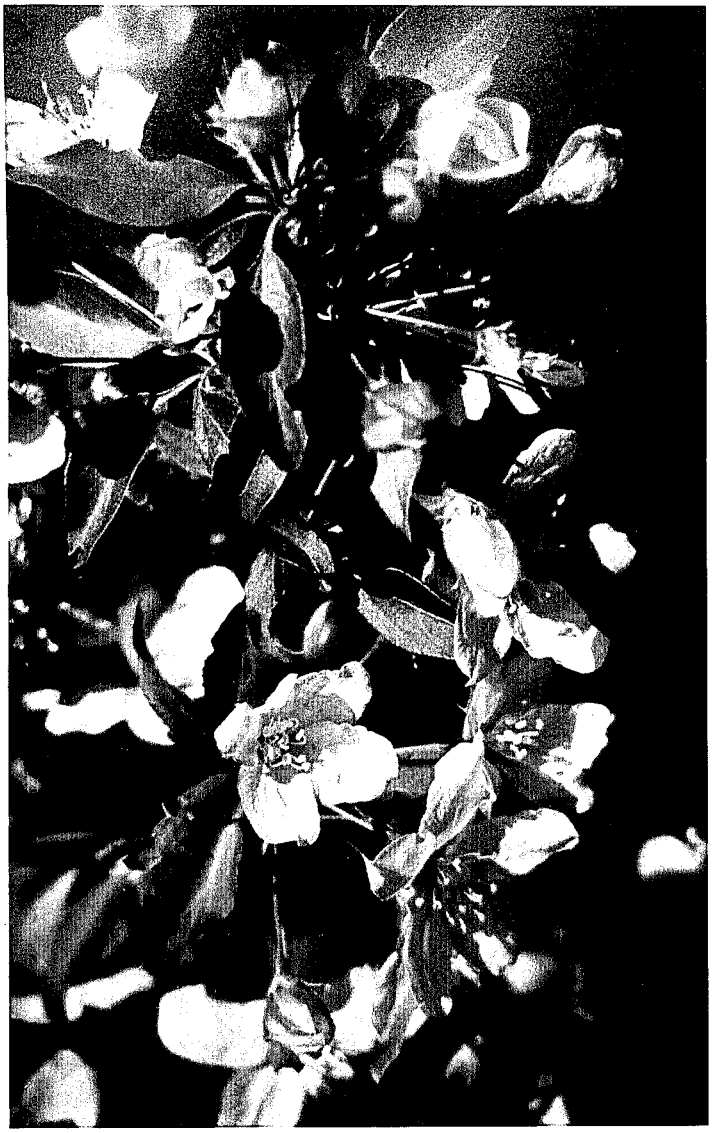

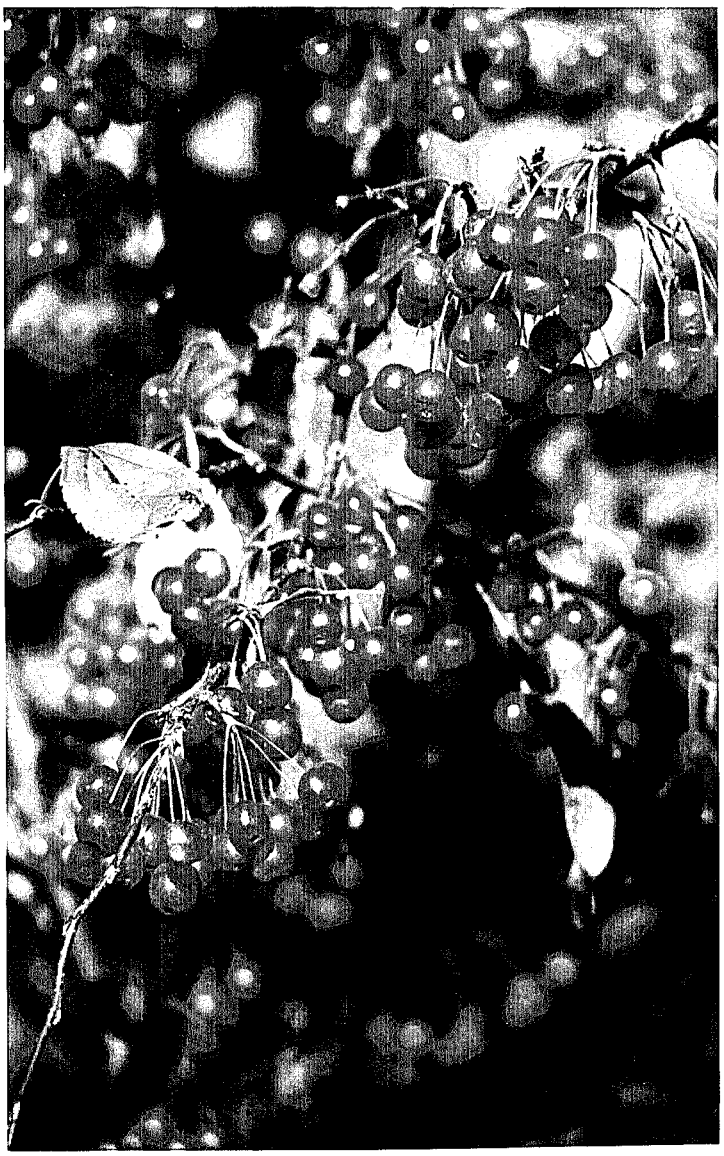

* * * * *